(12) United States Patent
Schlatter et al.

(10) Patent No.: US 9,827,137 B2
(45) Date of Patent: Nov. 28, 2017

(54) DEVICES FOR TREATING BRUXISM (71) Applicant: SJS GROUP, LLC, Winona Lake, IN (US)

(72) Inventors: Daniel Schlatter, Warsaw, IN (US); Justin James May, Leesburg, IN (US); Scott Steffensmeier, Winona Lake, IN (US)

(73) Assignee: SJS GROUP, LLC, Winona Lake, IN (US)

( * ) Notice: Subject to any disclaimer, the term of this patent is extended or adjusted under 35 U.S.C. 154(b) by 174 days.

(21) Appl. No.: 14/440,793

(22) PCT Filed: Nov. 5, 2013

(86) PCT No.: PCT/US2013/068519
§ 371 (c)(1),
(2) Date: May 5, 2015

(87) PCT Pub. No.: WO2014/074519
PCT Pub. Date: May 15, 2014

(65) Prior Publication Data
US 2015/0297390 A1 Oct. 22, 2015

Related U.S. Application Data

(60) Provisional application No. 61/722,865, filed on Nov. 6, 2012.

(51) Int. Cl.
*A61B 5/00* (2006.01)
*A61F 5/56* (2006.01)

(52) U.S. Cl.
CPC ............ *A61F 5/566* (2013.01); *A61B 5/4557* (2013.01); *A61B 5/486* (2013.01); *A61B 5/682* (2013.01);
(Continued)

(58) Field of Classification Search
CPC .... A61F 5/566; A61F 2005/563; A61B 5/486; A61B 5/682; A61B 5/4557; A61B 5/7405
See application file for complete search history.

(56) References Cited

U.S. PATENT DOCUMENTS 3,532,091 A    10/1970 Lerman
4,257,408 A *  3/1981 Ramey .................. A63H 3/001
                                                          601/46
(Continued)

FOREIGN PATENT DOCUMENTS

WO    2008061328 A2    5/2008

OTHER PUBLICATIONS

EP Search Report for European Application No. EP13853546.6.
International Search Report of PCT/US2013/068519, dated Apr. 3, 2014, Applicant: Jace Medical, LLC, 3 pages.

*Primary Examiner* — Max Hindenburg
(74) *Attorney, Agent, or Firm* — Seyfarth Shaw LLP; Joseph M. Walker; Brian Michaelis (57) ABSTRACT

The present disclosure relates to devices that aid a user in ceasing bruxism. The devices may be placed between a user's teeth, such as during sleep, and alert the user when the user clenches his/her teeth. In an aspect, a device includes a housing containing a battery power source, a vibration device, and an electrical contact mechanism having a movable element which closes a circuit to actuate the vibration device. A disk-shaped portion adapted to be emplaced in a person's mouth between a cheek and adjacent teeth is disposed around the housing. A resilient bite portion extends from the housing and is adapted to be emplaced between upper and lower teeth. A compressible element is disposed in the bite portion and causes the movable element of the electrical contact to close to actuate the vibration device in response to compression of the bite portion.

12 Claims, 12 Drawing Sheets (52) U.S. Cl.
CPC .......... *A61B 5/7405* (2013.01); *A61B 5/7455* (2013.01); *A61F 5/56* (2013.01); *A61B 2560/0214* (2013.01); *A61B 2562/0247* (2013.01); *A61B 2562/164* (2013.01); *A61B 2562/168* (2013.01); *A61B 2562/227* (2013.01); *A61F 2005/563* (2013.01)

(56) References Cited

U.S. PATENT DOCUMENTS

| | | | | |
|---|---|---|---|---|
| 4,348,178 | A | * 9/1982 | Kurz | A61C 7/008 433/5 |
| 5,078,153 | A | 1/1992 | Nordlander | |
| 5,586,562 | A | 12/1996 | Matz | |
| 6,089,864 | A | 7/2000 | Buckner et al. | |
| 6,544,199 | B1 | * 4/2003 | Morris | A61B 5/11 600/590 |
| 6,613,001 | B1 | 9/2003 | Dworkin | |
| 6,890,239 | B2 | * 5/2005 | Kopelle | A63H 3/28 434/236 |
| 7,137,393 | B2 | * 11/2006 | Pivovarov | A61F 5/566 128/848 |
| 7,890,193 | B2 | * 2/2011 | Tingey | A61N 1/36014 607/134 |
| 8,690,800 | B2 | * 4/2014 | Lillydahl | A61B 5/0488 600/546 |
| 8,931,486 | B2 | * 1/2015 | Halstrom | A61F 5/566 128/848 |
| 8,961,437 | B2 | * 2/2015 | Al-Tawil | G06F 3/011 600/590 |
| 9,028,250 | B2 | * 5/2015 | Spaulding | A61C 7/00 433/147 |
| 2010/0036286 | A1 | 2/2010 | Scholz | |

\* cited by examiner

DEVICES FOR TREATING BRUXISM

CROSS REFERENCES TO RELATED APPLICATIONS

This application claims the benefit of U.S. Provisional Patent Application Ser. No. 61/722,865, entitled BIOFEEDBACK DEVICE FOR TREATING BRUXISM, filed on Nov. 6, 2012, the content of which is incorporated herein by reference in its entirety.

FIELD

The present disclosure relates to devices for treating bruxism.

BACKGROUND

Biofeedback is a process which uses instruments to provide information about an activity which allows a user to change his/her behavior relative to that activity. Bruxism is a reflexive chewing activity, such as teeth clenching or grinding. When conscious attention is distracted, such as during sleeping, subconscious processes can run unchecked, allowing bruxism to occur. Bruxism can result in tooth decay and costly corrective dental procedures.

SUMMARY

The present disclosure relates to devices that aid a user in ceasing bruxism. The devices may be placed between a user's teeth, such as while the user is sleeping or awake, and alert the user when the user clenches his/her teeth. In general, the devices include a circuit that, when completed, such as by the user clenching his/her teeth, causes a vibration mechanism to activate and cause a sensation which signals the user to stop clenching his/her teeth.

In an aspect, a dental appliance for detecting and treating teeth clenching is disclosed. The device may include a first housing containing a power source, such as a battery, a vibration device connected to the power source, and an electrical contact mechanism having a movable element which closes a circuit to actuate the vibration device. A disk-shaped portion may be disposed around the first housing and is adapted to be emplaced in a person's mouth between a cheek and adjacent teeth. A resilient bite portion extends from the first housing and is adapted to be emplaced between upper and lower teeth. The bite portion may have an interior area which is compressible, such as by upper and lower teeth moving toward each other. A compressible element may be disposed in the interior area. The compressible element may cause the movable element of the electrical contact to close to actuate the vibration device in response to compression of the bite portion.

The compressible element may be an elongated stiff part that extends within the bite portion and has an end with a part that engages the movable element as a lever end. The elongated stiff part causes the lever end to apply a force to the movable element to thereby close the circuit in response to compression, for example caused by a user clenching his/her teeth.

The compressible element may be a substantially u-shaped piece having opposed elongated stiff arms and a base, wherein the base is bendable outwardly when the arms are moved toward one another. In this aspect, the base presses the movable element to thereby close the circuit in response to being bent outwardly.

The compressible element may be an encapsulated medium that is adapted to bulge toward the movable element to close the circuit in response to compression, for example causes by a user clenching his/her teeth. The medium may be a gas, a liquid, a soft solid, small beads, or any combination thereof.

In an aspect, a dental appliance for detecting and treating teeth clenching may include a first housing adapted to fit between a person's inner cheek and adjacent upper and lower rows of teeth, wherein the housing has an interior chamber. A power source, a signal generator powered by the power source, and a signal generator powered by the power source are disposed within the chamber. A resilient bite portion extends from the first housing and is adapted to be emplaced between upper and lower teeth. The bite portion also has an interior area which is compressible, as by upper and lower teeth moving toward each other, to actuate the signal generator to generate a signal. A responsive device is in communication with the signal generator which responds to the signal.

The device may include an electrical contact mechanism having a movable element adapted to close a circuit to operate the signal generator, and the signal may be an electrical current which powers the responsive device. The responsive device provides a sensory indication to the person, for example, the sensory indication may be an audible sound, a physical sensation, such as a vibration, and any combination of audible and physical sensations. In an aspect, the responsive device is a vibrator that engages part of the person's body, and is actuated in response to a signal indicative of a teeth clenching threshold force value. The vibration caused by the vibrator may vary with the force of teeth clenching.

The device may include a compressible element disposed in the interior area and adapted to engage the movable element. The compressible element causes the movable element to physically move to close the circuit in response to being compressed. In an aspect, the compressible element may be a substantially u-shaped piece having opposed elongated stiff arms and a base, wherein the base is bendable outwardly in response to the arms being moved toward one another. When the base is bent outwardly, it presses the movable element to thereby close the circuit. In another aspect, the compressible element may be an encapsulated medium adapted to bulge toward the movable element to close the circuit in response to being compressed.

In an aspect, a device may include an outer wall defining an inner chamber. The outer wall may include a disc portion and a tab or bite portion, and the inner chamber extends within both of the disc portion and the tab portion. A vibrator and electrical conductors are carried within the inner chamber, and an actuating member extends within the portion of the inner chamber defined by the tab portion. The electrical conductors activate the vibrator in response to the actuating member being deformed, for example by a user biting the tab portion.

In an aspect, a device may include an outer wall defining an inner chamber. The outer wall may include a disc portion and a tab or bite portion, and the inner chamber extends within both of the disc portion and the tab portion. A housing is carried within the inner chamber, and houses or encapsulates a battery, a vibrator and electrical conductors. The housing may also include a thinned portion or diaphragm portion. A pair of arms are joined to the housing and flank the thinned portion. The arms extend within the portion of the inner chamber defined by the tab portion. When a user compresses or bites on the tab portion, the arms move toward one another causing the thinned portion to deform and activate the vibrator. Thus, the vibrator is activated in response to the arms moving toward one another.

In another aspect, a device may include an outer wall defining an inner chamber. The outer wall may include a disc portion and a tab or bite portion, and the inner chamber extends within both of the disc portion and the tab portion. A housing is carried within the inner chamber, and houses or encapsulates a battery, a vibrator and electrical conductors. The housing may also include a thinned portion or diaphragm portion. An elongate member extends within the portion of the inner chamber defined by the tab portion. The thinned portion deforms, thereby activating the vibrator in response to the elongate member being deformed, for example by a user biting the tab portion.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which.

DETAILED DESCRIPTION

Detailed embodiments of devices, systems, and methods are disclosed herein, however, it is to be understood that the disclosed embodiments are merely exemplary of the devices, systems, and methods, which may be embodied in various forms. Therefore, specific functional details disclosed herein are not to be interpreted as limiting, but merely as a basis for the claims and as a representative basis for teaching one skilled in the art to variously employ the present disclosure.

Figure 1:
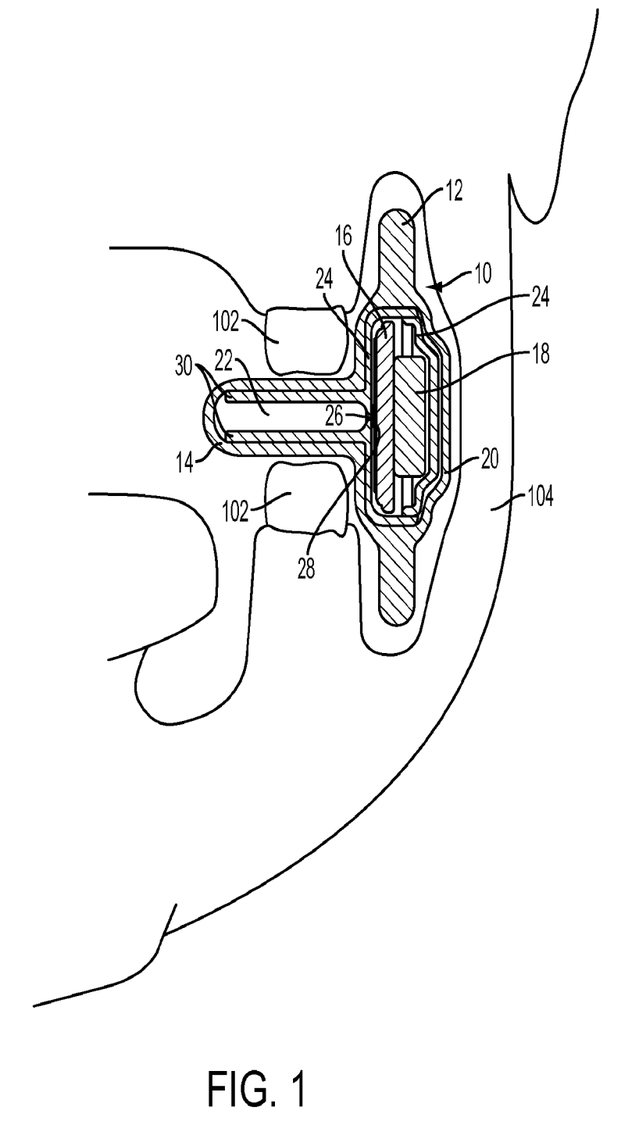
FIG. 1 illustrates a sectional side view of a device of the present disclosure as shown in a user's mouth.
Figure 2A:
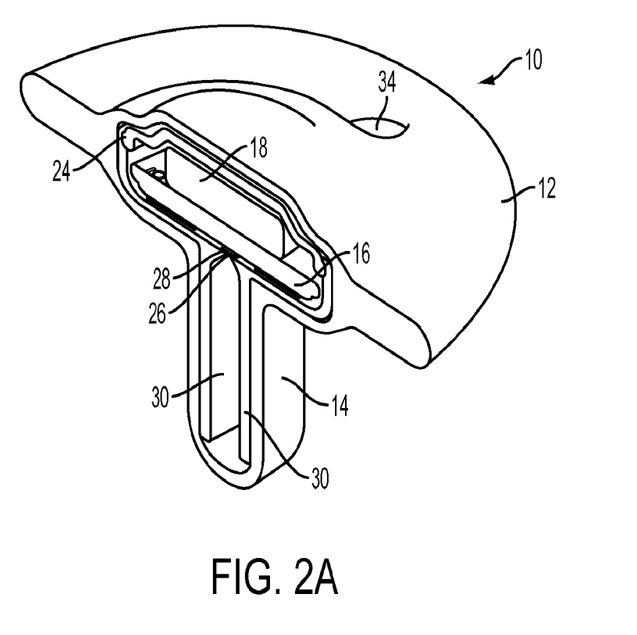
FIG. 2A illustrates a perspective sectional view of the device of FIG. 1.
Figure 2B:
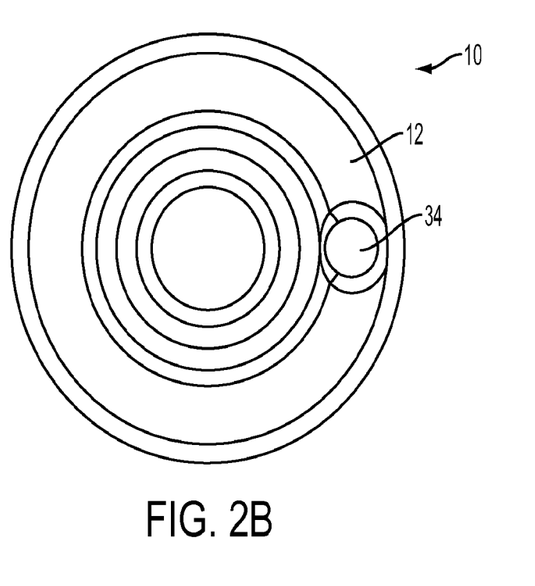
FIG. 2B illustrates a top view of the device of FIG. 2A.
Figure 2C:
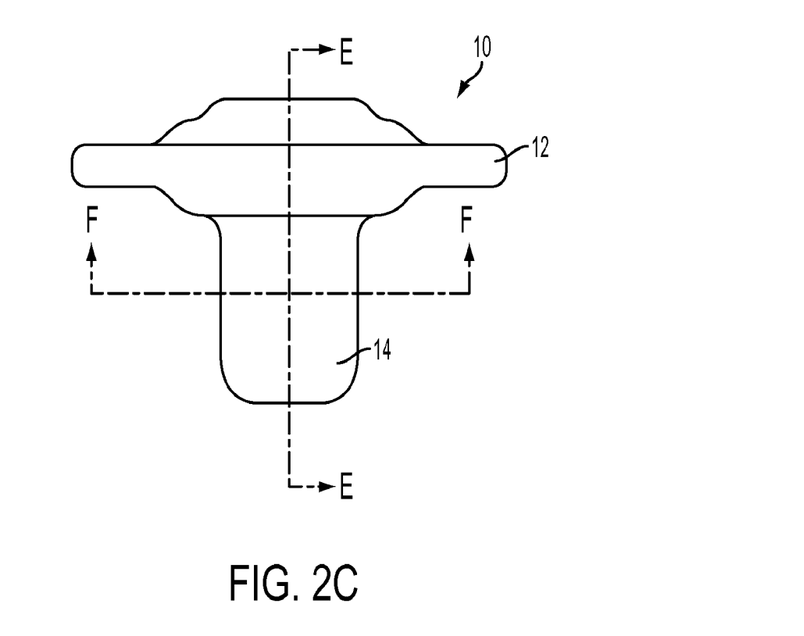
FIG. 2C illustrates a side view of the device of FIG. 2A.
Figure 2D:
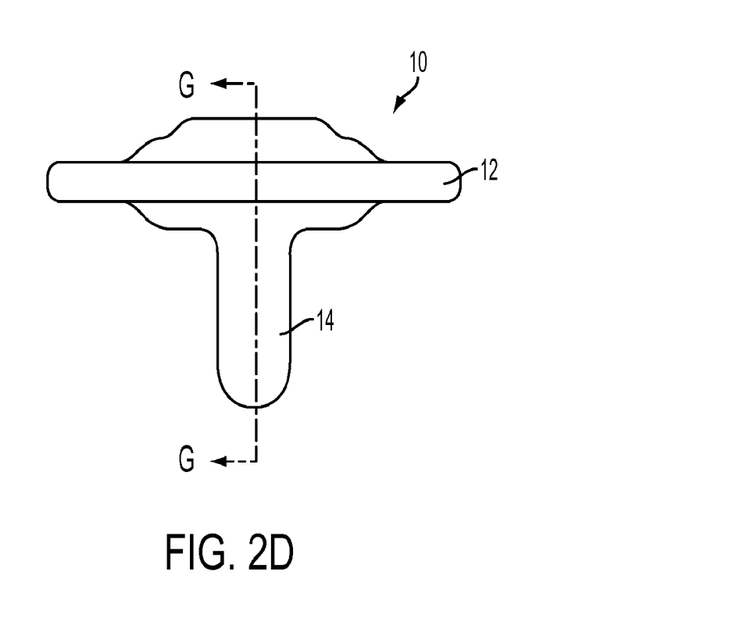
FIG. 2D illustrates another side view of the device of FIG. 2A.
Figure 2E:
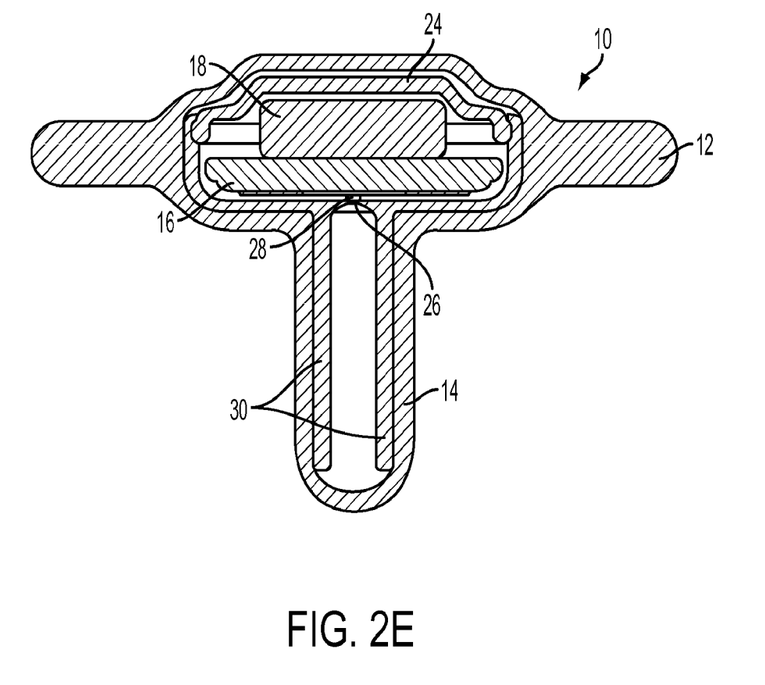
FIG. 2E illustrates a sectional side view of the device of FIG. 2C, as taken along line E-E.
Figure 2F:
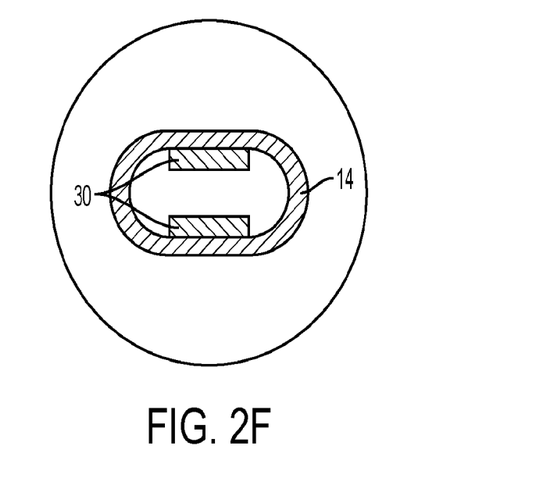
FIG. 2F illustrates a sectional bottom view of the device of FIG. 2C, as taken along line F-F.
Figure 2G:
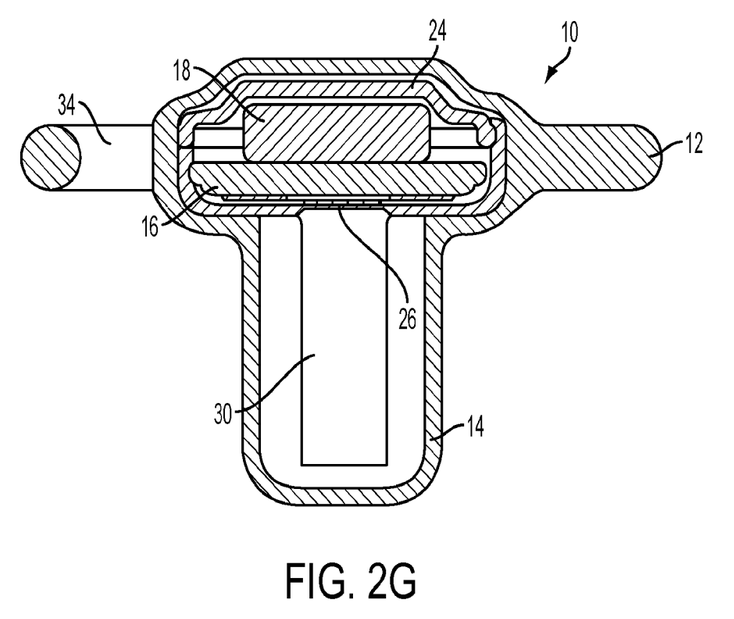
FIG. 2G illustrates a sectional side view of the device of FIG. 2D, as taken along line G-G.

FIGS. 1-2G illustrate a device 10 adapted to provide a signal/sensory indication to a user in response to the user clenching his/her jaw, or clenching or grinding his/her teeth 102, for example during bruxism, according to an aspect of the disclosure. The device 10 may be used as a training device that provides a reminder to the user in the form of a vibration sensation, an audible sound, an olfactory sensation, a visual indication, a taste sensation, or other sensory indication in response to the physical activity of teeth clenching or bruxism. As illustrated in FIG. 1, the device 10 includes a disc-shaped portion 12 shaped and formed to nest between a cheek 104 and adjacent teeth 102. The device 10 also includes a bit portion or tab 14 that extends and is adapted to situate between the user's teeth 102. When the user clenches his/her teeth 102 the user places pressure on the tab 14.

The disc-shaped portion 12 and the tab 14 or bite portion are shaped to both maintain patient comfort while anchoring the device 10 in the user's mouth at an optimal position for proper function. For example, the disc-shaped portion 12 is shaped to comfortably fit between the user's cheek 104 and teeth 102, and allows the device 10 to maintain position in the user's cheek pocket. Similarly, the length of the tab 14 is designed to prevent the device 10 from being pushed out from between the user's teeth 102 into the user's cheek pocket, and to limit interference with the user's tongue.

The tab 14 is compressible and includes a mechanism that when compressed activates electronic components in the disc portion of the device 10. When activated, the electronic components (for example, including a power source, such as battery 16, and a responsive device, such as vibrator 18) deliver a vibrating sensation to the user. This vibration sensation provides a signal, such as a biofeedback signal, to the user of teeth clenching and allows the user to take corrective action. The cessation of clenching quickly becomes a natural and automatic response to the vibration reminder. In this way, the device 10 provides a biofeedback response useful in training the user to correct teeth clenching/bruxism.

The device 10 may be formed having a continuous outer wall 20, such outer wall 20 formed from a deformable material, preferably medical grade silicone, such that when a user clenches his/her teeth 102 the tab 14 deforms. Outer wall 20 defines an inner chamber 22 which is formed within both the disc-shaped portion 12 and the tab 14. A housing 24 is carried in inner chamber 22, such housing encapsulating the vibrator 18 and the battery 16. The housing 24 completely surrounds the battery 16 and the vibrator 18 such that if outer wall 20 is pierced or otherwise ruptures, the battery and the vibrator will remain encapsulated. The housing 24 is preferably formed in two parts which snap together to allow assembly of the battery 16 and vibrator 18 and associated electrical conductors prior to enclosing the housing in the outer wall 20.

A diaphragm or thinned section 26 is formed in housing 24 on the face of the housing which is oriented in the direction of tab 14. The thinned section 26 is shaped such that it repeatably bends or deforms in the same direction, namely in the direction of battery 16. The thinned section 26 is bendable or deformable and facilitates activation of the vibrator 18 as described below. In this embodiment, the thinned section 26 is a single crease in housing 24. A contact element, for example, electrical conductors 28 or a signal generator, which are in electrical communication with vibrator 18, are mounted to housing 24 proximate the inner side of thinned section 26. Battery 16 is positioned adjacent electrical conductor 28, such that when a user is not clenching his/her teeth, electrical conductor is spaced from battery 16. When a user does clench his/her teeth, thinned section 26 bends, thereby pushing or moving the electrical conductor 28 against battery 16 which completes a circuit, allows a signal to flow to vibrator 18, and causes vibrator 18 to activate. As such, when tab 14 is not deformed, a gap is present between electrical conductor 28 and battery 16, which gap is bridged by movement of thinned section 26 which is facilitated by deformation of tab 14.

Tab 14 has a generally elongate cross-section, such as an oval-shaped cross-section. This elongate shape helps to orient biofeedback device 10 between the teeth, wherein the device 10 will tend to naturally rotate such that the longer axis of the tab 14 will orient generally parallel with the user's teeth.

Disc-shaped portion 12 is formed having an aperture 34 passing therethrough, such that aperture 34 forms a hole through the outer flange portion of biofeedback device 10. Aperture 34 does not provide access to internal chamber 22, since this would allow saliva and other fluids to potentially spoil the internal electronics. Instead, aperture 34 allows air to pass through biofeedback device 10 in the case where biofeedback device 10 becomes lodged in the user's airway. In this way, aperture 34 is a safety feature which prevents suffocation.

In one embodiment, a pair of elongate arms 30 extend from housing 24, wherein the arms are spaced on either side of thinned section 26. Arms 30 extend within internal chamber 22 in tab 14. Arms 30 are positioned parallel one another. Arms 30 are wider than they are thick, such that a space is formed between the arms when tab 14 is not clenched. When tab 14 is clenched, arms 30 are forced toward each other which causes thinned section 26 to deform and to push electrical conductor 28 against battery 16. The arms 30 are preferably oriented parallel with the longer axis of tab 14, such that a user's bite motion will cause the arms 30 to move toward each other, rather than biting on the edges of the arms.

As described above, the device 10 uses a lever-type mechanism, which has one or more elongated elements, arms 30, in the bite area that, when moved toward the longitudinal axis of the bite area, cause a movement of the contact element, electrical conductor 28, so as to close a circuit and thereby generate a signal. Such a signal can be an electrical current, to actuate the vibrator 18, for example. In one such embodiment described, there are two elongated arms 30 connected through a base, thinned section 26, of what constitutes a u-shaped piece. As the arms 30 bend toward one another under influence of teeth moving toward engagement (clenching), the base flexes. The base flexes outwardly (essentially bulging), to thereby move the contact element to close a circuit. The base could just as easily move inwardly, and thereby lever the contact to a closed position.

Figure 3A:
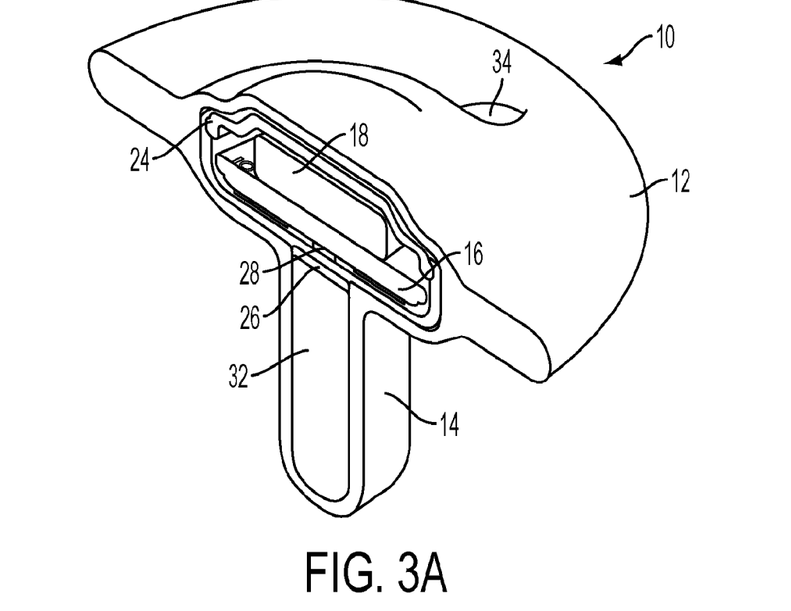
FIG. 3A illustrates a perspective sectional view of a device of the present disclosure.
Figure 3B:
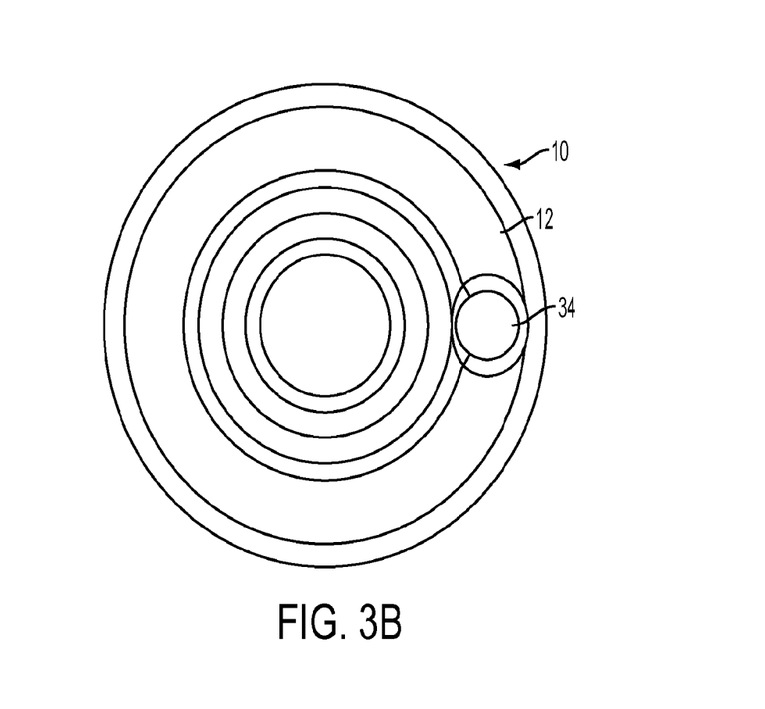
FIG. 3B illustrates a top view of the device of FIG. 3A.
Figure 3C:
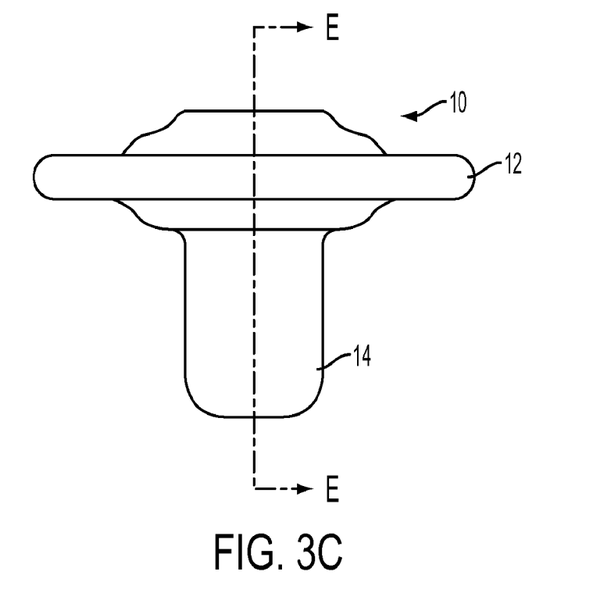
FIG. 3C illustrates a side view of the device of FIG. 3A.
Figure 3D:
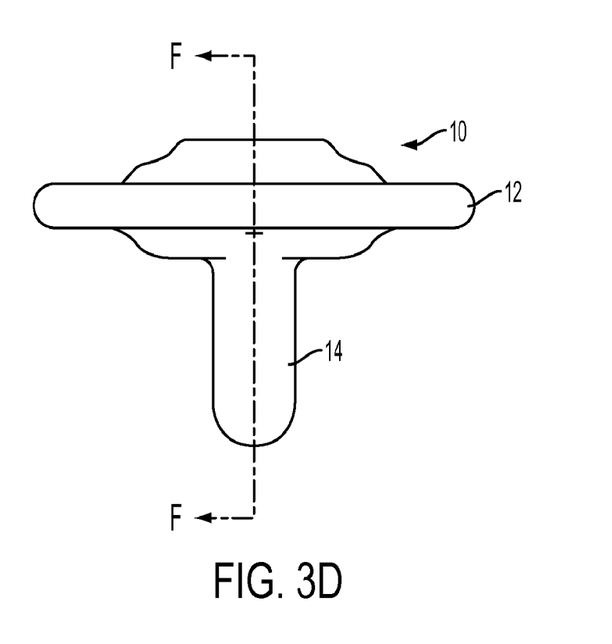
FIG. 3D illustrates another side view of the device of FIG. 3A.
Figure 3E:
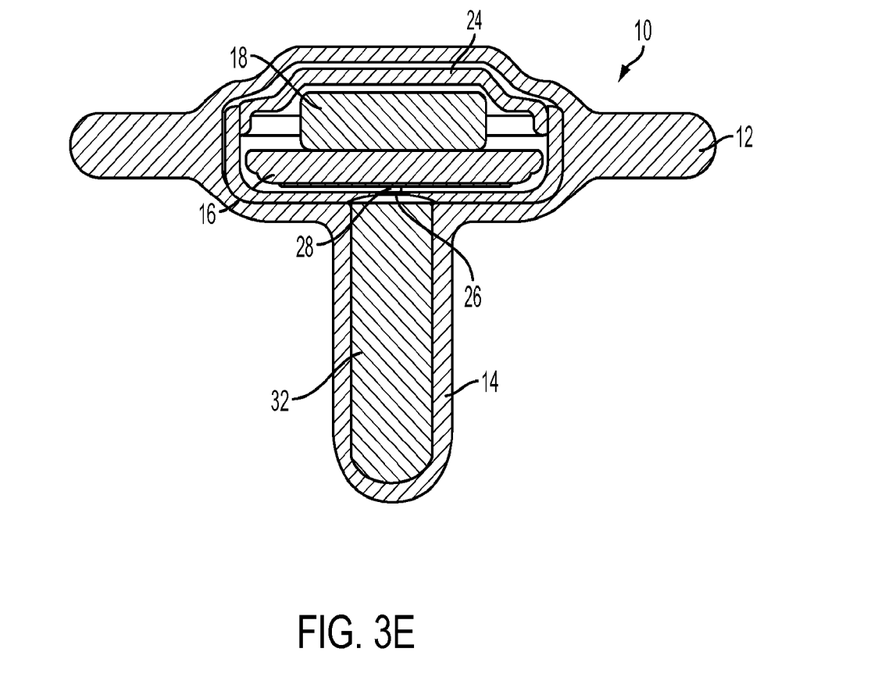
FIG. 3E illustrates a sectional side view of the device of FIG. 3C, as taken along line E-E.
Figure 3F:
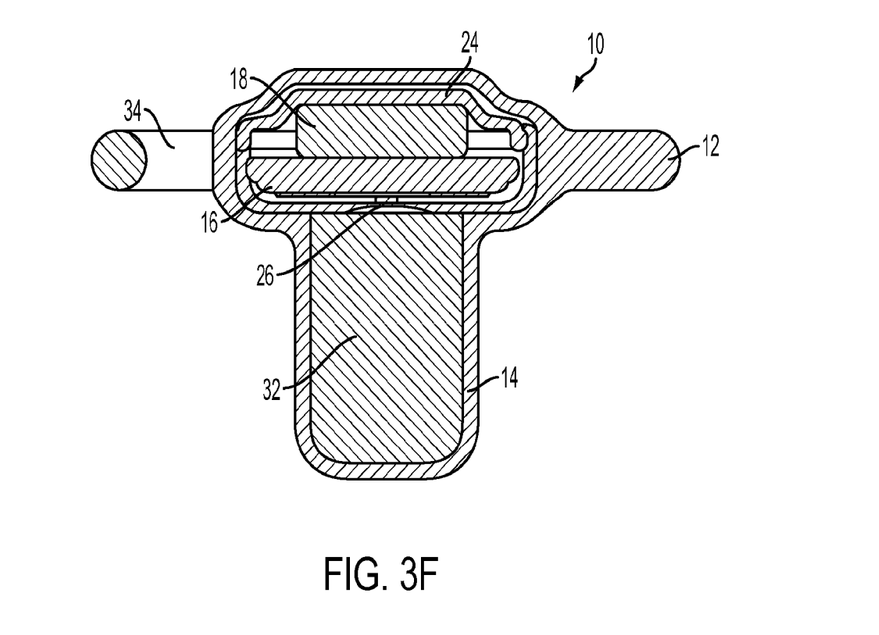
FIG. 3F illustrates a sectional side view of the device of FIG. 3D, as taken along line F-F.
Figure 3G:
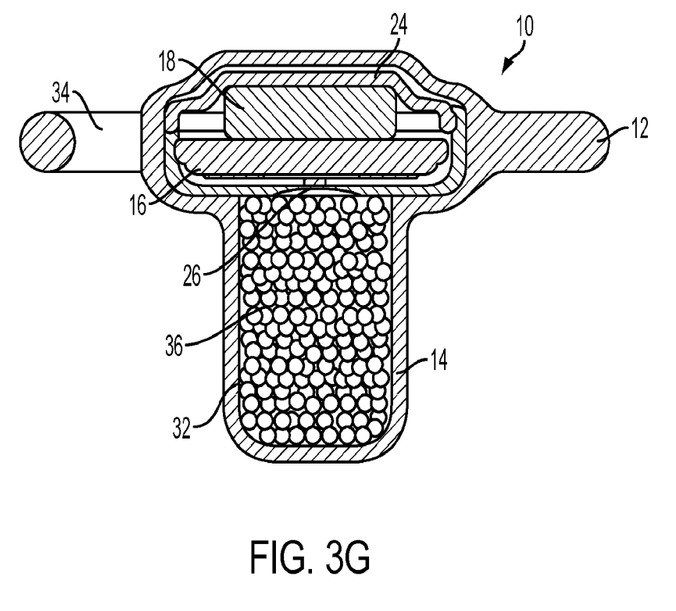
FIG. 3G illustrates a sectional side view of the device of FIG. 3D, as taken along line F-F including beads as a compressible medium.

In an additional embodiment, illustrated and described with reference to FIGS. 3A-3G, an elongate member 32 substantially fills the portion of inner chamber 22 in tab 14. Elongate member 32 is formed from a deformable medium such that as a user bites on tab 14, the elongate member 32 deforms or bulges in the direction of the diaphragm or thinned section 26, which causes electrical conductors 28 to contact battery 16, thereby activating vibrator 18. The medium encapsulated within the resilient bite area region, chamber 22, expands laterally (orthogonally relative to the upper and lower rows of teeth), as the area, tab 14, is compressed, the medium pushes the contact element, electrical conductors 28, to close the circuit. The medium can thus be of many kinds, such as a gas, a liquid, or a deformable solid (as illustrated in FIGS. 3E and 3F), or some other material which is squeezable, such as tiny beads 36 (as illustrated in FIG. 3G).

The embodiments described above are very similar in concept in that a bulging movement physically engages the contact element to close a circuit. One of elongate member 32 or elongate arms 30 defines an actuating member. Actuating member is such that, when a user bites tab 14, the actuating member is actuated in a way that completes a circuit and activates vibrator 18. Housing 24 is optional, the electrical components may be placed directly within inner chamber 22 and actuated directly by the actuating member.

Figure 4:
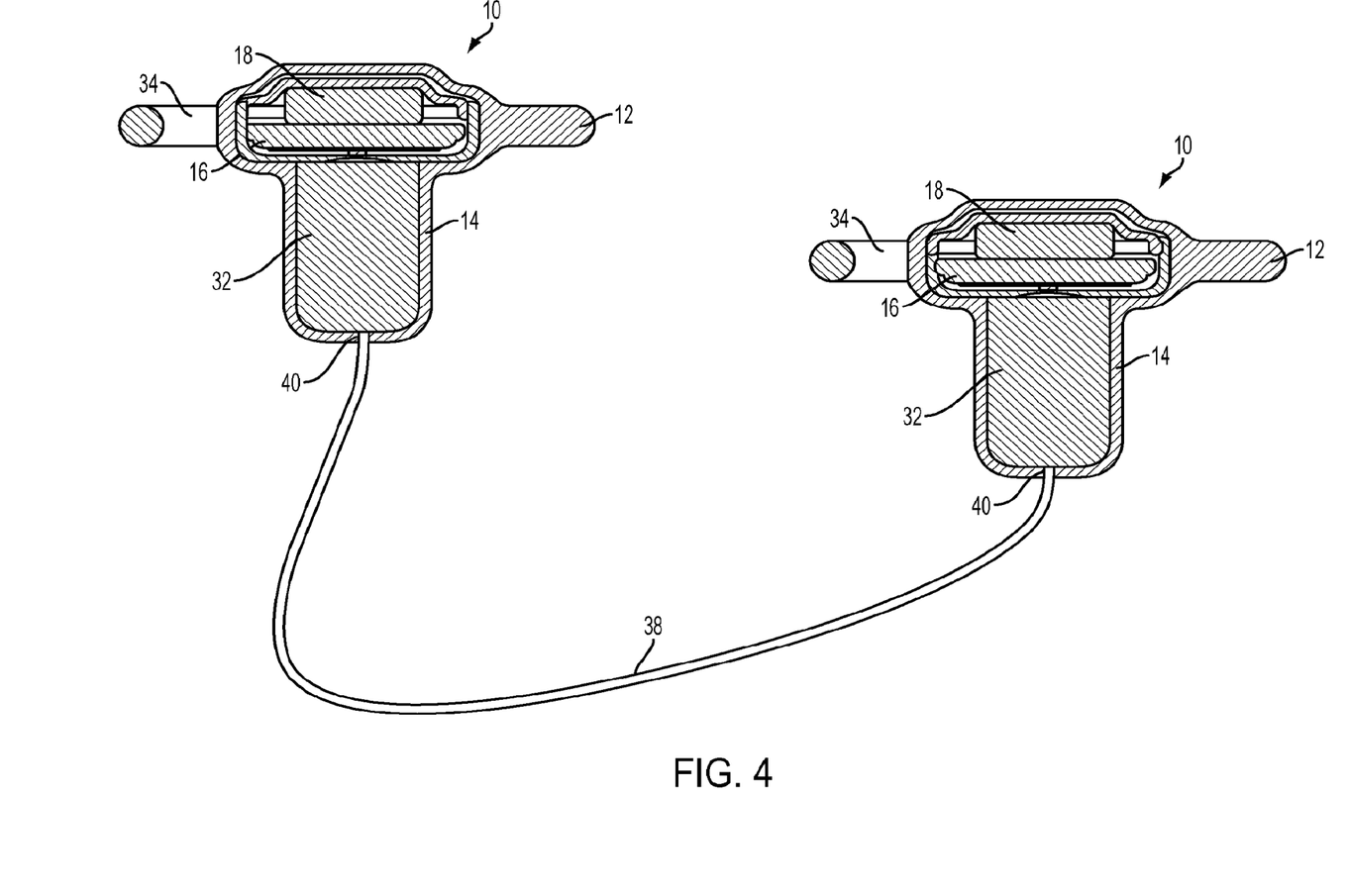
FIG. 4 illustrates a sectional view of a dual device of the present disclosure including two of the devices of FIG. 3A.

The devices 10 described above, involves a single integrated unit which is emplaced in a person's cheek. All of the electronics, power source and indicator device for providing an impulse to the user of teeth clenching (e.g., a vibrator), are contained in that integrated unit. However, it is contemplated that two such units or devices 10 may be desirable, if for no other reason than a symmetrical balance in a person's mouth. As illustrated in FIG. 4, first and second devices 10 are interconnected. Such an interconnected arrangement could use a simple electrical connection between the devices 10 (one in one cheek, one in the other), or a pneumatic connection whereby a threshold force value in one device 10 can close a circuit in the other device 10 (that is, the two units do not have to be identical, but operate as an integrated system).

As illustrated in FIG. 4, the first and second devices 10 are interconnected by a tube 38 that provides fluid (liquid or gas) communication between the two devices 10, via apertures 40. In this embodiment, compression of the tab 14 on either device may cause the vibrator 18 to activate. It should also be appreciated that only one of the devices 10 may include the electrical contacts 28, power source 16 and vibrator 18. In this aspect, a threshold force value in one device 10 can close the circuit in the other device 10.

Figure 5:
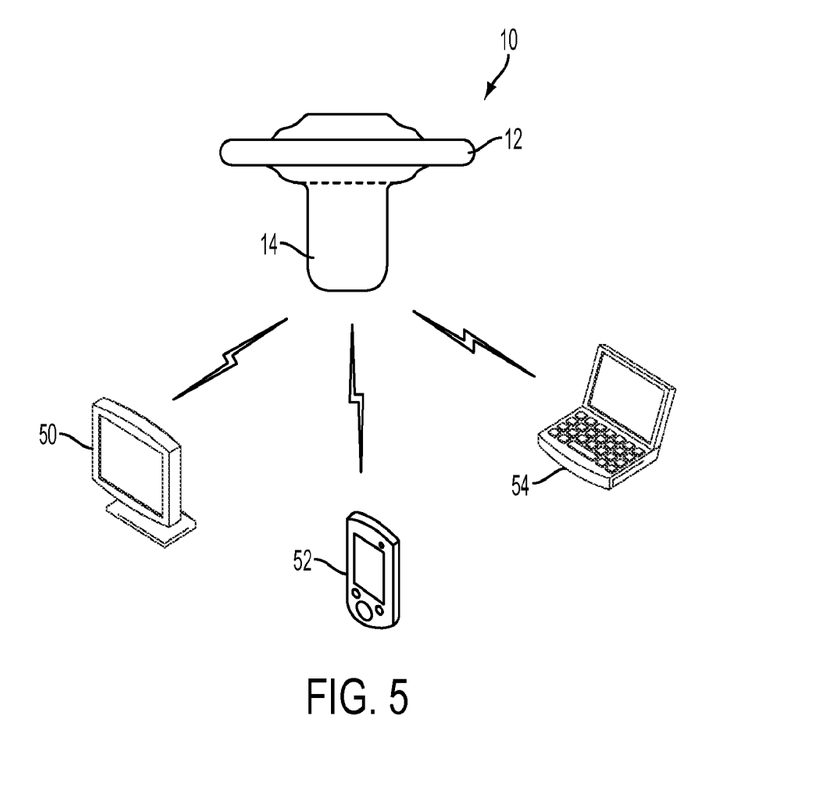
FIG. 5 illustrates a device of the present disclosure communicating with a user device.

The embodiments are not limited to an integrated device 10 with all operational elements located in a person's cheek. As illustrated in FIG. 5, the clenching action may result in a signal transmitted, such a through Bluetooth, infrared or radio frequency communication, from the action of the bite area to a remote station or device, such as a computer 50, a mobile phone or handheld device 52, or a laptop computer 54, which then provides some stimulus to the person. The stimulus could be an visual stimulus, audible sound or alarm, for example, or it could be another physical stimulus, such as a vibration through some mechanism engaging or attached to a person, but which is remote from the general housing of the device 10. Additionally, the device 10 may include circuitry adapted to receive and transmit data and other information to the remote station or device. For example, the device 10 may transmit data relating to force of bite, frequency of teeth clenching, and other monitoring information for recordation, without any immediate biofeedback to the person.

Figure 6:
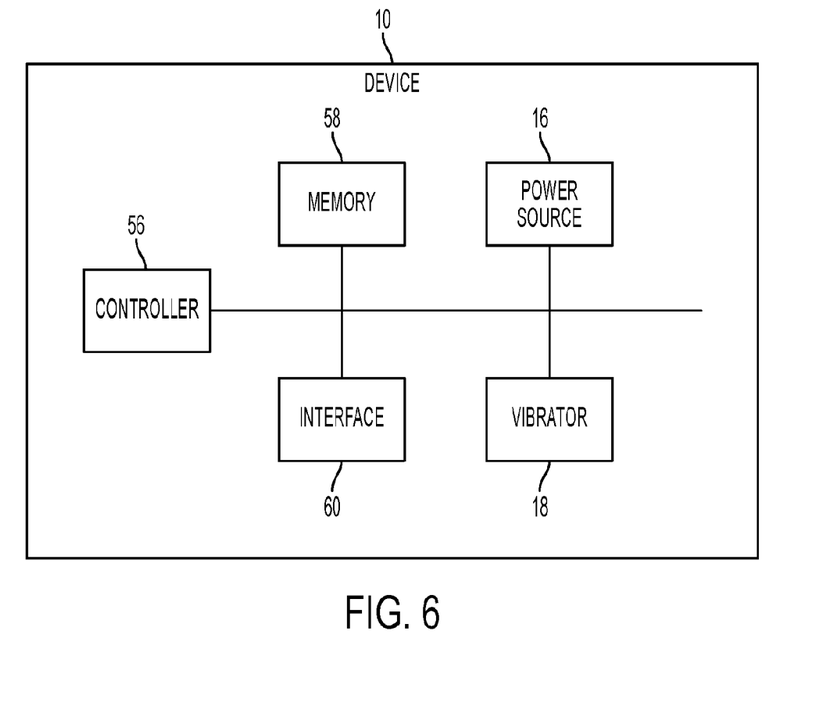
FIG. 6 illustrates a block diagram of circuitry of a device of the present disclosure.

A functional block diagram of components of the device 10 are described with reference to FIG. 6. As illustrated in FIG. 6, the device 10 may include a controller 56 and a memory 58 coupled to the controller 56. The device 10 also includes interface circuitry 60 which may include, for example, a universal serial bus (USB) port, Firewire port, infrared data transmitter, radio frequency data transmitter, Bluetooth, or other communication technique. The interface 60 allows the device 10 to communicate with other devices, such as, the computer 50, mobile phone or handheld device 52, or laptop computer 54 illustrated in FIG. 5. The interface 60 may also be used to power or charge the power source or battery 16 of the device 10.

The interface 60 and memory 58 may be coupled to the controller 56 by one or more internal signal paths. The controller 56 may be a processor, a control circuit, etc., and may facilitate communication between various components of the device 10 and control operation of various electrical components of the device 10. In one aspect, the memory 58 can store data or computer programs for use with the device 10. For example, the memory 58 may be used to store instructions for the vibrator 18. It is contemplated that the biofeedback may be proportional, in some respect, to the amount of teeth-clenching that is occurring (i.e., the force being applied to the bite portion, tab 14). Accordingly, as the force applied by the closing teeth increases, the stimulus (i.e. vibration by the vibrator 18) applied to the user likewise increases. Additionally, controls can be provided to allow the user to adjust how the system will respond. These could be amplitude adjustments as indicated in the preceding paragraph, whereby the impulse to the user varies with clenching force.

For example, the device 10 may have one or more settings relating to duration, amplitude, etc. of the vibration. The device 10 may use usage input to modify the input into a variety of outputs based on the settings. The setting could be based on clinical data, guess and check, patient demographics, etc. As an example, one bite for 1 second could trigger 2 seconds of vibratory output. In another example, the vibration may have a sinusoidal decay to ease the user back to sleep. These settings may be programmed by the user via the computing device(s) illustrated in FIG. 5, or even based on activating the vibrator in a certain sequence to enter a 'setup' mode. The device 10 can then emit a vibration to the user to communicate that it has or has not received the inputs when in 'setup' mode.

The memory 58 can also store data relating to a use of the device 10. For example, the memory 58 may record duration of teeth clenching, pressure/force of teeth clenching, time, intensity, etc., to create a log or history of the teeth clenching of the user. This data may then be uploaded or transmitted to one or more of the computing devices illustrated in FIG. 5. Without limitation, the memory 58 can include a non-transitory computer-readable recording medium, such as a hard drive, DVD, CD, flash drive, volatile or non-volatile memory, RAM, or any other type of data storage, for example.

Although the devices, systems, and methods have been described and illustrated in connection with certain embodiments, many variations and modifications will be evident to those skilled in the art and may be made without departing from the spirit and scope of the disclosure. For example, the vibrator may be a piezoelectric device, a linear actuator, etc. Similarly, the trigger mechanism for causing the vibrator to activate may be a pressure sensitive switch or a contact switch. The discourse is thus not to be limited to the precise details of methodology or construction set forth above as such variations and modification are intended to be included within the scope of the disclosure. Moreover, unless specifically stated any use of the terms first, second, etc. do not denote any order or importance, but rather the terms first, second, etc. are merely used to distinguish one element from another.

What is claimed is:

1. A dental device, comprising:
   an outer wall defining an inner chamber, said outer wall having a disc portion adapted to be emplaced in a person's mouth between a cheek and adjacent teeth, and a tab portion, adapted to be emplaced between upper and lower teeth, said inner chamber extending within both said disc portion and said tab portion;
   a housing carried within said inner chamber, said housing encapsulating a battery, a vibrator and electrical conductors, said housing including a thinned portion; and
   an elongate member extending within the portion of said inner chamber defined by said tab portion, wherein said thinned portion deforms based on the upper and lower teeth moving toward each other and activates said vibrator in response to said elongate member being deformed.

2. A dental device, comprising:
   an outer wall defining an inner chamber, said outer wall having a disc portion adapted to be emplaced in a person's mouth between a cheek and adjacent teeth, and a tab portion, adapted to be emplaced between upper and lower teeth, said inner chamber extending within both said disc portion and said tab portion;
   a vibrator and electrical conductors carried within said inner chamber; and
   an actuating member extending within the portion of said inner chamber defined by said tab portion, wherein said electrical conductors activate said vibrator in response to said actuating member being deformed based on the upper and lower teeth moving toward each other.

3. A dental appliance for detecting and treating teeth clenching, comprising:
   a first housing containing a battery power source, a vibration device connected to said power source, and an electrical contact mechanism having a movable element which closes a circuit to actuate said vibration device;
   a disk-shaped portion around said first housing and adapted to be emplaced in a person's mouth between a cheek and adjacent teeth;
   a resilient bite portion extending from said first housing and adapted to be emplaced between upper and lower teeth, said bite portion having an interior area which is compressible, as by upper and lower teeth moving toward each other; and
   a compressible element disposed in said interior area, said compressible element causing said movable element of said electrical contact to close to actuate said vibration device in response to compression of said bite portion.

4. The dental appliance of claim 3, wherein said compressible element engages said movable element in response to said compression.

5. The dental appliance of claim 4, wherein said compressible element causes said movable element to physically move to close said circuit in response to said compression.

6. The dental appliance of claim 5, wherein said compressible element is an encapsulated medium adapted to bulge toward said movable element to close said circuit in response to said compression.

7. The dental appliance of claim 6, wherein said medium is a gas.

8. The dental appliance of claim 6, wherein said medium is a liquid.

9. The dental appliance of claim 6, wherein said medium is a soft solid.

10. The dental appliance of claim 6, wherein said medium is small beads.

11. A dental appliance for detecting and treating teeth clenching, comprising:
- a first housing adapted to fit between a person's inner cheek and adjacent upper and lower rows of teeth, said housing having an interior chamber;
- a disk-shaped portion around said first housing and adapted to be emplaced in said person's mouth between said cheek and adjacent teeth;
- a power source within said chamber;
- a signal generator within said chamber powered by said power source;
- a resilient bite portion extending from said first housing and adapted to be emplaced between upper and lower teeth, said bite portion having an interior area which is compressible, as by upper and lower teeth moving toward each other, to actuate said signal generator to generate a signal; and
- a responsive device in communication with said signal generator which responds to said signal.

12. The dental appliance of claim 11, wherein said chamber is part of a second housing isolated from and within said first housing so as to prevent any liquid from said person's mouth from ordinarily entering said chamber, said power source and said signal generator being within said chamber, and wherein said responsive device is a vibrator which engages part of said person's body, said vibrator being actuated in response to a signal indicative of a teeth clenching threshold force value and powered by said power source, said vibrator also being within said chamber.

* * * * *